US008691840B2

(12) United States Patent
Flessner et al.

(10) Patent No.: US 8,691,840 B2
(45) Date of Patent: *Apr. 8, 2014

(54) N-BIARYLAMIDES

(75) Inventors: Timo Flessner, Wuppertal (DE);
Frank-Gerhard Böss, Berkshire (GB);
Frank-Thorsten Hafner, Wuppertal (DE); Joachim Luithle, Wülfrath (DE);
Christoph Methfessel, Wuppertal (DE);
Leila Telan, Wuppertal (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/235,743

(22) Filed: Sep. 19, 2011

(65) Prior Publication Data

US 2012/0157490 A1 Jun. 21, 2012

Related U.S. Application Data

(60) Continuation of application No. 12/099,108, filed on Apr. 7, 2008, now Pat. No. 8,030,329, which is a division of application No. 10/565,181, filed as application No. PCT/EP2004/008037 on Jul. 19, 2004, now Pat. No. 7,354,930.

(30) Foreign Application Priority Data

Jul. 30, 2003 (DE) .................................. 103 34 724

(51) Int. Cl.
*A01N 43/90* (2006.01)
*A61K 31/44* (2006.01)

(52) U.S. Cl.
USPC .......................................... 514/305

(58) Field of Classification Search
USPC ........................................... 514/305
See application file for complete search history.

(56) References Cited

U.S. PATENT DOCUMENTS 3,579,523 A 5/1971 Sandberg et al.
5,998,429 A 12/1999 Macor et al.

FOREIGN PATENT DOCUMENTS

DE 10162442 A1 7/2003
WO WO-03078431 A1 9/2003

OTHER PUBLICATIONS

Muhammad et al., Stroke; A journal of cerebral circulation, (Mar. 2011) vol. 42, No. 3, pp. 783-791.*
Dineley et al., The Journal of Neuroscience, "B-amyloid activities the mitogen-activated protein kinase cascade via hippocampal alpha7 nicotinic acetylcholine receptors: in vitro and in vivo mechanism related to Alzheimer's disease", 2001, vol. 21, pp. 4125-4133.
Thinschmidt et al., Brain Research, (Apr. 8, 2008) vol. 1203, pp. 51-60.
Muhammad et al., Stroke: a journal of cerebral circulation, (Mar. 2011) vol. 42, No. 3, pp. 783-791.

* cited by examiner

*Primary Examiner* — Niloofar Rahmani
(74) *Attorney, Agent, or Firm* — Edwards Wildman Palmer LLP; Ralph A. Loren; Nicholas J. DiCeglie, Jr.

(57) ABSTRACT

The invention relates to N-biarylamides useful for the prophylaxis and/or treatment of impairments of perception, concentration, learning and/or memory, and to processes for preparing them, and pharmaceutical compositions containing them.

5 Claims, No Drawings

N-BIARYLAMIDES

The invention relates to N-biarylamides, to a process for the preparation thereof and to the use thereof for producing medicaments for the treatment and/or prophylaxis of diseases and for improving perception, concentration, learning and/or memory.

Nicotinic acetylcholine receptors (nAChR) form a large family of ion channels which are activated by the messenger acetylcholine which is produced in the body (Galzi and Changeux, *Neuropharmacol.* 1995, 34, 563-582). A functional nAChR consists of five subunits which may be different (certain combinations of α1-9 and β1-4,γ,δ,ε subunits) or identical (α7-9). This leads to the formation of a diversity of subtypes which differ in the distribution in the muscles, the nervous system and other organs (McGehee and Role, *Annu. Rev. Physiol.* 1995, 57, 521-546). Activation of nAChR leads to influx of cations into the cell and to stimulation of nerve cells or muscle cells. Selective activation of individual nAChR subtypes restricts this stimulation to the cell types which have the corresponding subtype and is thus able to avoid unwanted side effects such as, for example, stimulation of nAChR in the muscles. Clinical experiments with nicotine and experiments in various animal models indicate that central nicotinic acetylcholine receptors are involved in learning and memory processes (e.g. Rezvani and Levin, *Biol. Psychiatry* 2001, 49, 258-267). Nicotinic acetylcholine receptors of the alpha7 subtype (α7 nAChR) have a particularly high concentration in regions of the brain which are important for learning and memory, such as the hippocampus and the cerebral cortex (Séguéla et al., *J. Neurosci.* 1993, 13, 596-604). The α7 nAChR has a particularly high permeability for calcium ions, increases glutamatergic neurotransmission, influences the growth of axons and, in this way, modulates neuronal plasticity (Broide and Leslie, *Mol. Neurobiol.* 1999, 20, 1-16).

Certain quinuclidinecarboxanilides are described as antiarrhythmics and local anesthetics (cf., for example, FR 1.566.045, GB 1 578 421 and Oppenheimer et al. *Life Sci.* 1991, 48, 977-985).

WO 01/60821 discloses biarylcarboxamides with affinity for the α7 nAChR for the treatment of learning and perception impairments.

WO 03/043991, WO 93/055878 and WO 04/013136 disclose quinuclidinamine derivatives and WO 03/051874, WO 03/078431 and DE 10162442.5 disclose quinuclidine acid derivatives which are suitable as α7-nAChR agonists for the treatment of learning and perception impairments.

The present invention relates to compounds of the formula

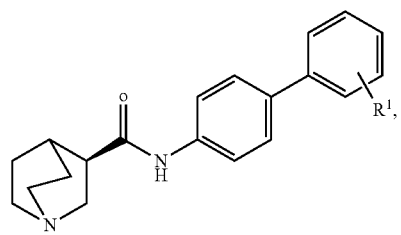

(I)

in which
R$^1$ is a group of the formula —NR$^2$—CO—NR$^3$R$^4$, —NR$^2$—CO—CO—OR$^5$, —NH—SO$_2$R$^6$, —SO$_2$NHR$^7$ or —NH—CO—R$^8$, where
R$^2$ is hydrogen or C$_1$-C$_6$-alkyl, R$^3$ and R$^{4'}$ are independently of one another hydrogen, C$_1$-C$_6$-alkyl, C$_3$-C$_8$-cycloalkyl or phenyl, which is optionally substituted by up to 3 radicals independently of one another selected from the group of halogen, cyano, C$_1$-C$_6$-alkyl, C$_1$-C$_6$-alkoxy, trifluoromethyl and trifluoromethoxy, or
R$^3$ and R$^4$ together with the nitrogen atom to which they are bonded form a 5- to 6-membered heterocyclyl,
R$^5$ is hydrogen; C$_1$-C$_6$-alkyl, C$_3$-C$_8$-cycloalkyl or aryl, where C$_1$-C$_6$-alkyl is optionally substituted by aryl,
R$^6$ is C$_1$-C$_6$-alkyl, C$_3$-C$_8$-cycloalkyl, 5- to 6-membered heterocyclyl, aryl or 5- to 6-membered heteroaryl, where C$_1$-C$_6$-alkyl is optionally substituted by aryl,
R$^7$ is hydrogen, C$_1$-C$_6$-alkyl, C$_3$-C$_8$-cycloalkyl, 5- to 6-membered heterocyclyl, aryl or 5- to 6-membered heteroaryl, where C$_1$-C$_6$-alkyl is optionally substituted by aryl,
R$^8$ is C$_3$-C$_8$-cycloalkyl, C$_1$-C$_6$-alkyl or phenyl, where C$_1$-C$_6$-alkyl is substituted by C$_1$-C$_6$-alkoxy and phenyl by 1 to 3 radicals independently of one another selected from the group of halogen, cyano, C$_1$-C$_6$-alkoxy, trifluoromethyl and trifluoromethoxy,
and the salts, solvates and solvates of the salts thereof.

Compounds of the invention are the compounds of the formula (I) and the salts, solvates and solvates of the salts thereof; the compounds which are encompassed by formula (I) and have the formulae mentioned hereinafter and the salts; solvates and solvates of the salts thereof, and the compounds which are encompassed by formula (I) and are mentioned hereinafter as exemplary embodiments and the salts, solvates and solvates of the salts thereof, where the compounds which are encompassed by formula (I) and are mentioned hereinafter are not already salts, solvates and solvates of the salts.

The compounds of the invention may, depending on their structure, exist in stereoisomeric forms (enantiomers, diastereomers). The invention therefore relates to the enantiomers or diastereomers and respective mixtures thereof. The stereoisomerically pure constituents can be isolated in a known manner from such mixtures of enantiomers and/or diastereomers.

The compounds of the invention may also be in the form of the salts, solvates or solvates of the salts thereof.

Salts which are preferred for the purposes of the invention are physiologically acceptable salts of the compounds of the invention.

Physiologically acceptable salts of the compounds of the invention may be acid addition salts of the compounds with mineral acids, carboxylic acids or sulfonic acids. Particularly preferred examples are salts with hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, propionic acid, lactic acid, tartaric acid, citric acid, fumaric acid, maleic acid or benzoic acid.

However, salts which may be mentioned are also salts with, conventional bases, such as, for example, alkali metal salts (e.g. sodium or potassium salts), alkaline earth metal salts (e.g. calcium or magnesium salts) or ammonium salts derived from ammonia or organic amines such as, for example, diethylamine, triethylamine, ethyldiisopropylamine, procaine, dibenzylamine, N-methylmorpholine, dihydroabiethylamine, 1-ephenamine or methylpiperidine.

Solvates is the term used for the purposes of the invention for those forms of the compounds which form a complex with solvent molecules by coordination in the solid or liquid state. Hydrates are a special form of solvates in which the coordination takes place with water.

In addition, the present invention also encompasses prodrugs of the compounds of the invention. The term "prodrugs" encompasses compounds which themselves may be biologically active or inactive but are converted (for example by metabolism or hydrolysis) to compounds of the invention during their residence time in the body.

For the purposes of the present invention, the substituents generally have the following meaning:

Aryl stands for naphthyl or phenyl, preferably phenyl.

$C_1$-$C_6$- and $C_1$-$C_4$-alkoxy stands for a straight-chain or branched alkoxy radical respectively having 1 to 6 and 1 to 4 carbon atoms. Preference is given to a straight-chain or branched alkoxy radical having 1 to 4, particularly preferably having 1 to 3, carbon atoms. The following may be mentioned by way of example and preferably: methoxy, ethoxy, n-propoxy, isopropoxy, tert.butoxy, n-pentoxy and n-hexoxy.

$C_1$-$C_6$- and $C_1$-$C_4$-alkyl stand for a straight-chain or branched alkyl radical respectively having 1 to 6 and 1 to 4 carbon atoms. Preference is given to a straight-chain or branched alkyl radical having 1 to 4, particularly preferably having 1 to 3, carbon atoms. The following may be mentioned by way of example and preferably: methyl, ethyl, n-propyl, isopropyl, tert.butyl, n-pentyl and n-hexyl.

$C_3$-$C_8$-, $C_3$-$C_6$- and $C_5$-$C_6$-cycloalkyl stand for cyclopropyl, cyclopentyl, cyclobutyl, cyclohexyl, cycloheptyl or cyclooctyl. Those which may be mentioned preferably are cyclopropyl, cyclopentyl and cyclohexyl and particularly preferably are cyclopentyl and cyclohexyl.

Halogen stands for fluorine, chlorine, bromine or iodine. Fluorine, chlorine and bromine are preferred. Fluorine and chlorine are particularly preferred.

5- to 6-membered heteroaryl stands for an aromatic radical having 5 to 6 ring atoms and up to 4, preferably up to 2, heteroatoms from the series S, O and/or N. The heteroaryl radical may be bonded via a carbon atom or heteroatom. The following may be mentioned by way of example and preferably: thienyl, furyl, pyrrolyl, thiazolyl, oxazolyl, imidazolyl, pyridyl, pyrimidinyl and pyridazinyl.

5- to 6-membered heterocyclyl stands for a heterocyclic radical having 5 to 6 ring atoms and up to 3, preferably 2, heteroatoms or hetero groups from the series N, O, S, SO, $SO_2$, with preference for N and O. The heterocyclyl radicals may be saturated or partially unsaturated. Saturated heterocyclyl radicals are preferred. The heterocyclyl radicals may be bonded via a carbon atom or a heteroatom. The following may be mentioned by way of example and preferably: pyrrolinyl, tetrahydrofuranyl, tetrahydrothienyl, pyranyl, piperidinyl, piperazinyl, thiopyranyl, morpholinyl.

When radicals in the compounds of the invention are optionally substituted, unless otherwise specified the radicals may have one or more identical or different substituents. Substitution by up to three identical or different substituents is preferred.

Preference is given to compounds of the formula (I) in which $R^1$ is a group of the formula —$NR^2$—CO—$NR^3R^4$, —$NR^2$—CO—CO—$OR^5$, —NH—$SO_2R^6$, —$SO_2NHR^7$ or —NH—CO—$R^8$, where $R^2$ is hydrogen or $C_1$-$C_4$-alkyl, $R^3$ and $R^4$ are independently of one another hydrogen, $C_1$-$C_4$-alkyl, $C_3$-$C_6$-cycloalkyl or phenyl, which is optionally substituted by up to 2 radicals independently of one another selected from the group of fluorine, chlorine, bromine, cyano, $C_1$-$C_4$-alkyl, $C_1$-$C_4$-alkoxy, trifluoromethyl and trifluoromethoxy, or $R^3$ and $R^4$ together with the nitrogen atom to which they are bonded form a 5- to 6-membered heterocyclyl, $R^5$ is hydrogen, $C_1$-$C_4$-alkyl, $C_3$-$C_6$-cycloalkyl, or aryl, where $C_1$-$C_4$-alkyl is optionally substituted by aryl, $R^6$ is $C_1$-$C_4$-alkyl, $C_3$-$C_6$-cycloalkyl, 5- to 6-membered heterocyclyl, aryl or 5- to 6-membered heteroaryl, where $C_1$-$C_4$-alkyl is optionally substituted by aryl, $R^7$ is hydrogen, $C_1$-$C_4$-alkyl, $C_3$-$C_6$-cycloalkyl, 5- to 6-membered heterocyclyl, aryl or 5- to 6-membered heteroaryl, where $C_1$-$C_4$-alkyl is optionally substituted by aryl, $R^8$ is $C_3$-$C_6$-cycloalkyl, $C_1$-$C_4$-alkyl or phenyl, where $C_1$-$C_4$-alkyl is substituted by $C_1$-$C_4$alkoxy and phenyl by 1 to 2 radicals independently of one another selected from the group of fluorine, chlorine, bromine, cyano, $C_1$-$C_4$-alkyl, $C_1$-$C_4$-alkoxy, trifluoromethyl and trifluoromethoxy, and the salts, solvates and solvates of the salts thereof.

Preference is likewise given to compounds of the formula (I) in which $R^1$ is a group of the formula —NH—CO—$NHR^3$, NH—CO—CO—OH, —NH—$SO_2R^6$, —$SO_2NHR^7$ or —NH—CO—$R^8$, where $R^3$ is hydrogen, $C_1$-$C_4$-alkyl, $C_5$-$C_6$-cycloalkyl or phenyl, which is optionally substituted by $C_1$-$C_4$-alkoxyl, $R^6$ is $C_1$-$C_4$-alkyl or phenyl, where $C_1$-$C_4$-alkyl is optionally substituted by phenyl, $R^7$ is hydrogen or $C_1$-$C_4$-alkyl which is optionally substituted by phenyl, $R^8$ is $C_5$-$C_6$-cycloalkyl, methoxymethyl or phenyl which is substituted by fluorine or chlorine, and the salts, solvates and solvates of the salts thereof.

Preference is likewise given to compounds of the formula

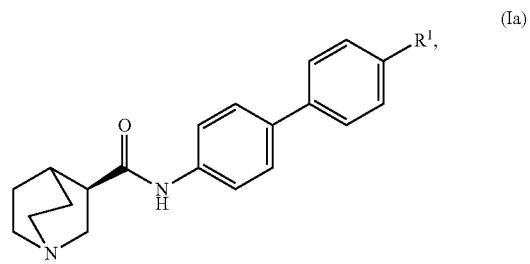

(Ia)

in which $R^1$ has the meanings indicated above, and the salts, solvates and solvates of the salts thereof.

Combinations of two or more of the abovementioned preferred ranges are very particularly preferred.

The invention further relates to a process for preparing the compounds of the invention, characterized in that

[A] compounds of the formula

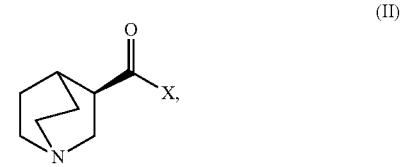

(II)

in which

X is hydroxy or a suitable leaving group such as, for example, chlorine or pentafluorophenoxy, are reacted with a compound of the formula

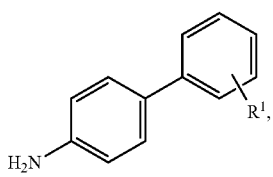

(III)

in which
R¹ has the abovementioned meanings,
in an inert solvent, where appropriate in the presence of a condensing agent and where appropriate in the presence of a base,
or
[B] compounds of the formula (II) initially are reacted with a compound of the formula

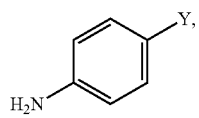

(IV)

in which
Y is a suitable leaving group such as, for example, triflate or halogen, preferably bromine or iodine,
where appropriate in an inert solvent, where appropriate in the presence of a condensing agent and where appropriate in the presence of a base to give compounds of the formula

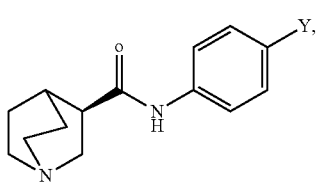

(V)

in which
Y has the abovementioned meanings,
and the latter are then reacted in a coupling reaction with compounds of the formula

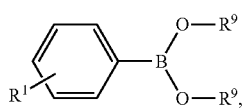

(VI)

in which
R¹ has the abovementioned meanings, and
R⁹ is hydrogen or methyl, or the two radicals together form a $CH_2CH_2$ or $C(CH_3)_2—C(CH_3)_2$ bridge,
in an inert solvent in the presence of a suitable catalyst and in the presence of a base,
and the resulting compounds of the invention are reacted where appropriate with the appropriate (i) solvents and/or (ii) bases or acids to give the solvates, salts and/or solvates of the salts thereof.

If X is a leaving group, preference is given to chlorine, mesyloxy and isobutyloxycarbonyloxy, in particular chlorine.

Examples of inert solvents for process steps (II)+(III)→(I) and (II)+(IV)→(V) are halohydrocarbons such as methylene chloride, trichloromethane, tetrachloromethane, trichloroethane, tetrachloroethane, 1,2-dichloroethane or trichloroethylene, ethers such as diethyl ether, methyl tert-butyl ether, dioxane, tetrahydrofuran, glycol dimethyl ether or diethylene glycol dimethyl ether, hydrocarbons such as benzene, xylene, toluene, hexane, cyclohexane or petroleum fractions, or other solvents such as nitromethane, ethyl acetate, acetone, dimethylformamide, dimethylacetamide, dimethyl sulfoxide, acetonitrile or pyridine. Dimethylformamide, tetrahydrofuran methylene chloride, or chloroform is preferred.

Condensing agents for process steps (II)+(III)→(I) and (II)+(IV)→(V) are, for example, carbodiimides such as, for example, N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethylpolystyrene (PS-carbodiimide) or carbonyl compounds such as carbonyldiimidazole, or 1,2-oxazolium compounds such as 2-ethyl-5-phenyl-1,2-oxazolium-3-sulfate or 2-tert-butyl-5-methylisoxazolium perchlorate, or acylamino compounds such as 2-ethoxy-1-ethoxycarbonyl-1,2-dihydroquinoline, or propanephosphonic anhydride, or isobutyl chloroformate, or bis(2-oxo-3-oxazolidinyl)phosphoryl chloride or benzotriazolyloxy-tri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or 0-(7-azabenzotriazol-1-yl)-N,N,N',N'-tetramethyluronium hexafluorophosphate (HATU) or benzotriazol-1-yloxyiris(dimethylamino)phosphonium hexafluorophosphate (BOP), or mixtures thereof.

It may be advantageous where appropriate to use these condensing agents in the presence of an auxiliary nucleophile such as, for example, 1-hydroxybenzotriazole (HOBt).

HATU or the combination of N-(3-dimethylaminoisopropyl)-N'-ethylcarbodiimide hydrochloride (EDC) and 1-hydroxybenzotriazole (HOBt) in dimethylformamide is particularly preferred.

Examples of bases for process steps (II)+(III)→(I) and (II)+(IV)→(V) are alkali metal carbonates such as, for example, sodium or potassium carbonate or bicarbonate, or organic bases such as trialkylamines, e.g. triethylamine, or N-methylmorpholine, N-methylpiperidine, 4-dimethylaminopyridine or diisopropylethylamine.

Process steps (II)+(III)→(I) and (II)+(IV)→(V) are preferably carried out in a temperature range from room temperature to 50° C. under atmospheric pressure.

Examples of inert solvents for process step (V)+(VI)→(I) are ethers such as dioxane, tetrahydrofuran or 1,2-dimethoxyethane, hydrocarbons such as benzene, xylene or toluene, or other solvents such as nitrobenzene, dimethylformamide, dimethylacetamide, dimethyl sulfoxide or N-methylpyrrolidone. Solvents such as, for example, dimethylformamide, dimethylacetamide, dimethyl sulfoxide or 1,2-dimethoxyethane are preferred.

Catalysts suitable for process step (V)+(VI)→(I) are for example palladium catalysts usual for Suzuki couplings, with preference for catalysts such as, for example, dichlorobis (triphenylphosphine)palladium, tetrakistriphenylphosphine-palladium, palladium(II) acetate or bis(diphenylphosphino) ferrocenepalladium(II) chloride (cf., for example, e.g. A.

Suzuki, *Acc. Chem. Res.* 1982, 15, 178ff; Miyaura et al., *J. Am. Chem. Soc.* 1989, 111, 314).

Bases suitable for process step (V)+(VI)→(I) are for example potassium acetate, cesium, potassium or sodium carbonate, barium hydroxide, potassium tert-butoxide, cesium fluoride or potassium phosphate. Cesium carbonate or sodium carbonate is preferred.

Process step (V)+(VI)→(I) is preferably carried out in a temperature range from room temperature to 130° C. under atmospheric pressure.

The compounds of the general formulae (II) and (VI) are known or can be synthesized by known processes from the appropriate precursors [cf., for example, for compounds of the general formula (II): Kato et al., *Chem. Pharm. Bull.* 1995, 43, 1351-1357; Orlek et al., *J. Med. Chem.* 1991, 34, 2726-2735; Plate et al., *Bioorg. Med. Chem.* 2000, 8, 449-454; for compounds of the general formula (VI): D. S. Matteson, in: *Stereodirected Synthesis with Organoboranes*, edited by K. Hafuer, C. W. Rees, B. M. Trost, J.-M, Lehn, P. v. Ragué Schleyer, Springer-Verlag, Heidelberg 1995; H. C. Brown, G. W. Kramer, A. B. Levy, M. M. Midland, *Organic Synthesis via Boranes*, Wiley, N.Y. 1975; A. Pelter, K. Smith, H. C. Brown, *Borane Reagent*, Academic Press, London 1988].

Compounds of the formulae (III) and (IV) are likewise known or can be synthesized by known processes from the appropriate precursors (cf., for example, *Comprehensive Heterocyclic Chemistry*, Katritzky et al., editors, Elsevier, 1996). Thus, for example, benzoic acid derivatives can be converted as shown in the following synthesis scheme by rearrangement (Curtius degradation) of the corresponding carbonyl azides into the corresponding aniline derivatives (cf., for example, S. Deprets, G. Kixsch, *Eur. J. Org. Chem.* 2000, 7, 1353ff):

Synthesis scheme

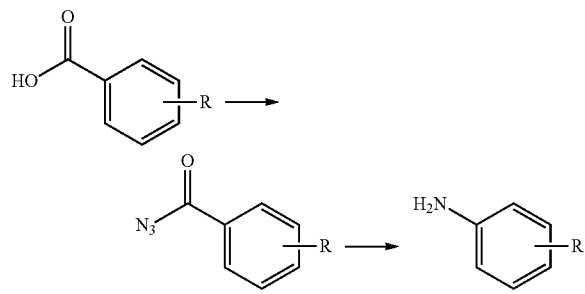

The compounds of the invention are suitable for use as medicaments for the treatment and/or prophylaxis of diseases in humans and/or animals.

The compounds of the invention show a valuable range of pharmacological effects which could not have been predicted.

They are notable as ligands, especially agonists, on the α7 nAChR.

The compounds of the invention can, because of their pharmacological properties, be employed alone or in combination with other medicaments for the treatment and/or prevention of cognitive impairments, especially of Alzheimer's disease. Because of their selective effect as α7 nAChR agonists, the compounds of the invention are particularly suitable for improving perception, concentration, learning or memory, especially after cognitive impairments like those occurring for example in situations/diseases/syndromes such as mild cognitive impairment, age-associated learning and memory impairments, age-associated memory loss, vascular dementia, craniocerebral trauma, stroke, dementia occurring after strokes (post-stroke dementia), post-traumatic craniocerebral trauma, general concentration impairments, concentration impairments in children with learning and memory problems, attention deficit hyperactivity disorder, Alzheimer's disease, Lewy body dementia, dementia with degeneration of the frontal lobes, including Pick's syndrome, Parkinson's disease, progressive nuclear palsy, dementia with corticobasal degeneration, amyotrophic lateral sclerosis (ALS), Huntington's disease, multiple sclerosis, thalamic degeneration, Creutzfeld-Jacob dementia, HIV dementia, schizophrenia, schizophrenia with dementia or Korsakoff's psychosis.

The present invention farther relates to a method for the treatment and/or prophylaxis of disorders, in particular the aforementioned disorders, by use of an effective amount of the compounds of the invention.

The compounds of the invention can be employed alone or in combination with other active ingredients for the prevention and treatment of the sequelae of neurodegenerative disorders. Preferred examples which may be mentioned of neurodegenerative disorders are Alzheimer's disease and Parkinson's disease.

The compounds of the invention can be employed alone or in combination with other medicaments for the prophylaxis and treatment of acute and/or chronic pain (for a classification, see "Classification of Chronic Pain, Descriptions of Chronic Pain Syndromes and Definitions of Pain Terins", 2nd edition, Meskey and Begduk, editors; IASP Press, Seattle, 1994), especially for the treatment of cancer-induced pain and chronic neuropathic pain like, for example, that associated with diabetic neuropathy, postherpetic neuralgia, peripheral nerve damage, central pain (for example as a consequence of cerebral ischemia) and trigeminal neuralgia, and other chronic pain such as, for example, lumbago, backache (low back pain) or rheumatic pain. In addition, these active ingredients are also suitable for the therapy of primary acute pain of any origin and of secondary states of pain resulting therefrom, and for the therapy of states of pain which were formerly acute and have become chronic.

The in vitro effect of the compounds of the invention can be shown in the following assays:

1. Determination of the Affinity of Test Substances for α7 nAChR by Inhibition of [$^3$H]-methyllycaconitine Binding to Rat Brain Membranes The [$^3$H]-methyllycaconitine binding assay is a modification of the method described by Davies et al. (*Neuropharmacol.* 1999, 38, 679-690).

Rat brain tissue (hippocampus or whole brain) is homogenized in homogenization buffer (10% w/v) (0.32 M sucrose, 1 mM EDTA, 0.1 mM phenylmethylsulfonyl fluoride (PMSF), 0.01% (w/v) NaN$_3$, pH 7.4, 4° C.) at 600 rpm in a glass homogenizer. The homogenate is centrifuged (1000×g, 4° C., 10 min) and the supernatant is removed. The pellet is resuspended (20% w/v) and the suspension is centrifuged (1000×g, 4° C., 10 min) The two supernatants are combined and centrifuged (15 000×g, 4° C., 30 min). This pellet is referred to as the P2 fraction.

The P2 pellet is washed twice with binding buffer (50 mM Tris-HCl, 1 mM MgCl$_2$, 120 mM NaCl, 5 mM KCl, 2 mM CaCl$_2$, pH 7.4), and centrifuged (15 000×g, 4° C., 30 min).

The P2 membranes are resuspended in binding buffer and incubated in a volume of 250 μl (amount of membrane protein 0.1-0.5 mg) in the presence of 1-5 nM [$^3$H]-methyllycaconitine, 0.1% (w/v) BSA (bovine serum albumin) and various concentrations of the test substance at 21° C. for 2.5 h. The non-specific binding is determined by incubation in the presence of 1 µM □-bungarotoxin or 100 µM nicotine or 10 µM MLA (methyllycaconitine).

The incubation is stopped by adding 4 ml of PBS (20 mM $Na_2HPO_4$, 5 mM $KH_2PO_4$, 150 mM NaCl, pH 7.4, 4° C.) and filtering through type A/E glass fiber filters (Gelman Sciences) which have previously been placed in 0.3% (v/v) polyethyleneimine (PEI) for 3 h. The filters are washed twice with 4 ml of PBS (4° C.), and the bound radioactivity is determined by scintillation measurement. All the assays are carried out in triplicate. The dissociation constant $K_i$ of the test substance was determined from the $IC_{50}$ of the compounds (concentration of the test substance at which 50% of the ligand bound to the receptor are displaced), the dissociation constant $K_D$ and the concentration L of [$^3$H]methyllycaconitine ($K_i = IC_{50}/(1+L/K_D)$).

In place of [$^3$H-]-methyllycaconitine it is also possible to employ other α7 nAChR-selective radioligands such as, for example, [$^{125}$]-α-bungarotoxin or nonselective nAChR radioligands together with inhibitors of other nAChRs.

Representative in vitro data for the effects of the compounds of the invention are shown in Table A:

TABLE A

| Example no. | $K_i$ [nM] |
|---|---|
| 2 | 2 |
| 5 | <1 |
| 7 | <1 |
| 11 | 16 |
| 15 | 27 |

The suitability of the compounds of the invention for the treatment of cognitive impairments can be shown in the following animal models:

2. Object Recognition Test

The object recognition test is a memory test. It measures the ability of rats (and mice) to distinguish between familiar and unfamiliar objects.

The test is carried out as described by Blokland et al., NeuroReport 1998, 9, 4205-4208; A. Ennaceur, J. Delacour, Behav. Brain Res. 1988, 31, 47-59; A. Ennaceur, K. Meliani, Psychopharmacology 1992, 109, 321-330; and Prickaerts et al., Eur. J. Pharmacol. 1997, 337, 125-136.

In a first run, a rat is confronted in an otherwise empty observation arena of relatively large size by two identical objects. The rat will investigate, i.e. sniff round and touch, both objects extensively. In a second run, after an interval of 24 hours, the rat is put in the observation arena again. One of the familiar objects has now been replaced by a new, unfamiliar object. If a rat recognizes the familiar object, it will concentrate on investigating the unfamiliar object. However, after 24 hours, a rat has normally forgotten which object it investigated in the first run, and it will therefore inspect both objects to the same extent. Administration of a substance with a learning- and memory-improving effect will lead to a rat recognizing the object seen in the first run 24 hours previously as familiar. It will investigate the new, unfamiliar object in more detail than the familiar one. This memory ability is expressed in a discrimination index. A discrimination index of zero means that the rat investigates both objects, the old and the new, for equal times; that is to say it has not recognized the old object and reacts to both objects as if they were unfamiliar and new. A discrimination index greater than zero means that the rat inspects the new object longer than the old one; that is to say the rat has recognized the old object.

3. Social Recognition Test:

The social recognition test is a test to examine the learning- or memory-improving effect of test substances.

Adult rats housed in groups are placed singly in test cages 30 minutes before the start of the test. Four minutes before the start of the test, the test animal is put in an observation box. After this adaptation time, a juvenile animal is put in with the test animal and the total time for which the adult animal investigates the juvenile animal is measured for 2 minutes (trial 1). All behaviors clearly directed at the young animal are measured, i.e. anogenital inspection, pursuit and grooming, during which the old animal is no further than 1 cm from the young animal. The juvenile animal is then taken out, and the adult is left in its test cage (for 24-hour retention, the animal is returned to its home cage). The test animal is treated with substance before or after the first test. Depending on the timing of the treatment, the learning or the storage of the information about the young animal can be influenced by the substance. After a fixed period (retention), the test is repeated (trial 2). A larger difference between the investigation times measured in trials 1 and 2 means that the adult animal has remembered the young animal better.

The compounds of the invention are suitable for use as medicaments for humans and animals.

The present invention also includes pharmaceutical preparations which, besides inert, nontoxic, pharmaceutically suitable excipients and carriers, contain one or more compounds of the invention, or which consist of one or more compounds of the invention, and to processes for producing these preparations.

The compounds of the invention are to be present in these preparations in a concentration of from 0.1 to 99.5% by weight, preferably from 0.5 to 95% by weight, of the complete mixture.

Besides the compounds of the invention, the pharmaceutical preparations may also contain other active pharmaceutical ingredients.

The abovementibned pharmaceutical preparations can be produced by known methods in a conventional way, for example using the excipient(s) or carrier(s).

The novel active ingredients can be converted in a known manner into conventional formulations such as tablets, coated tablets, pills, granules, aerosols, syrups, emulsions, suspensions and solutions, using inert, nontoxic, pharmaceutically suitable carriers or solvents. In these cases, the therapeutically active compound should in each case be present in a concentration of about 0.5 to 90% by weight of the complete mixture, i.e. in amounts which are sufficient to reach the stated dose range.

The formulations are produced for example by extending the active ingredients with solvents and/or carriers, where appropriate with use of emulsifiers and/or dispersants, it being possible for example when water is used as diluent where appropriate to use organic solvents as auxiliary solvents.

Administration takes place in a conventional way, preferably orally, trausdermally or parenterally, especially perlingually or intravenously. However, it can also take place by inhalation through the mouth or nose, for example with the aid of a spray, or topically via the skin.

It has generally proved advantageous to administer amounts of about 0.001 to 10 mg/kg, on oral administration preferably about 0.005. to 3 mg/kg, of body weight to achieve effective results.

It may, nevertheless, be necessary where appropriate to deviate from the stated amounts, in particular as a function of the body weight or of the mode of administration, of the individual behavior towards the medicament, the nature of its formulation and the time or interval over which administration takes place. Thus, it may be sufficient in some cases to make do with less than the aforementioned minimum amount, whereas in other cases the stated upper limit must be exceeded. Where larger amounts are administered, it may be advisable to divide these into a plurality of single doses over the day.

Abbreviations:

| | |
|---|---|
| conc. | concentrated |
| DAD | diode array detector |
| DCI | direct chemical ionization (in MS) |
| DMF | N,N-dimethylformamide |
| DMSO | dimethyl sulfoxide |
| ESI | electrospray ionization (in MS) |
| h | hour(s) |
| HPLC | high pressure/high performance liquid chromatography |
| LC-MS | coupled liquid chromatography-mass spectroscopy |
| min. | minute(s) |
| MS | mass spectroscopy |
| NMR | nuclear magnetic resonance spectroscopy |
| PBS | phosphate buffered saline |
| PdCl$_2$ (dppf) | bis(diphenylphosphaneferrocenyl)palladium(II) chloride |
| RT | room temperature (20° C.) |
| R$_t$ | retention time (in HPLC) |

HPLC and LC-MS Methods:
Method 1:
Instrument: HP 1100 with DAD detection; column: Kromasil RP-18, 60 mm×2 mm, 3.5 µm; eluent A: 5 ml HClO$_4$/L H$_2$O, eluent B: acetonitrile; gradient: 0 min 2% B, 0.5 min 2% B, 4.5 min 90% B, 6.5 min 90% B; flow rate: 0.75 ml/min; temperature: 30° C.; UV detection: 210 nm.

Method 2:
MS instrument type: Micromass ZQ; HPLC instrument type: Water Alliance 2790; column: Grom-Sil 120 ODS-4 BE 50 mm×2 mm, 3.0 µm; eluent B: acetonitrile +0.05% formic acid; eluent A: water +0.05% formic acid; gradient: 0.0 min 5% B→2.0 min 40% B→4.5 min 90% B→5.5 min 90% B; oven: 45° C.; flow rate: 0.0 min 0.75 ml/min→4.5 min 0.75 ml/min→5.5 min 1.25 ml/min; UV detection: 210 nm.

Method 3:
MS instrument type: Micromass ZQ; HPLC instrument type: HP 1100 series; UV DAD; column: Groin-Sil 120 ODS-4 HE 50 mm×2 mm, 3.0 µm; eluent A: water +500 µl of 50% formic acid/L, eluent B: acetonitrile +500 µl of 50% formic acid/L; gradient: 0.0 min 0% B 2.9 min 70% B 3.1 min 90% B→4.5 min 90% B; oven: 50° C.; flow rate: 0.8 ml/min; UV detection: 210 nm.

Starting Compounds:

EXAMPLE 1A (rac)-1-Azabicyclo[2.2.2]octane-3-carbonitrile

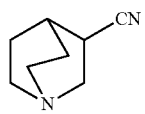

20.4 g (163 mmol) of 3-quinuclidinone and 41.4 g (212 mmol) of (4-toluenesulfonyl)methyl isocyanide are introduced into 435 ml of 1,2-dimethoxyethane and 16 ml of dry ethanol while cooling in ice. 45.7 g (407 mmol) of potassium tert-butoxide are slowly added in such a way that the temperature does not rise above 10° C. The mixture is then heated at 40° C. for 2.5 h. After cooling to RT, the resulting solid is filtered off. The filtrate is concentrated and chromatographed on neutral alumina (mobile phase: dichloromethane→ethyl acetate→ethyl acetate/methanol 50:1). 22.9 g (quant.) of the racemic product are obtained in slightly impure form.

EXAMPLE 2A (R)-1-Azabicyclo[2.2.2]octane-3-carbonitrile

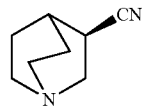

Enantiomer separation of the racemate from Example 1A takes place by HPLC on a chiral phase; [column: Daicel Chiralpak AD 250 mm×20 mm; eluent: 5% water, 87% acetonitrile, 8% acetonitrile with 2% diethylamine; flow rate: 10 ml/min; detection: 220 nm; volume injected: 0.3 ml]. 8.7 g of the title compound (87% of theory) are isolated from the separation of 20 g of racemic 1-azabicyclo[2.2.2]octane-3-carbonitrile.

R$_t$=6.19 min [Chiralpak AD 250 mm×4.6 mm, 10 µm; eluent: 5% water, 95% acetonitrile with 2% diethylamine; temperature: 30° C.; flow rate: 1.0 ml/min].

EXAMPLE 3A (R)-1-Azabicyclo[2.2.2]octane-3-carboxylic acid

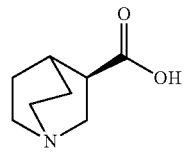 [SMILES: O=C(O)[C@H]1CN2CCC1CC2]

7.50 g (55.1 mmol) of (R)-1-azabicyclo[2.2.2]octane-3-carbonitrile (Example 2A) are heated together with 78 ml of conc. hydrochloric acid under reflux for 4 h. The solvent is removed under reduced pressure, and remaining water is removed by distillation with toluene several times. 12.9 g of the title substance, which still contains inorganic salts, are obtained and reacted without further purification.

EXAMPLE 4A (3R)—N-(4-Bromophenyl)-1-azabicyclo[2.2.2]octane-3-carboxamide

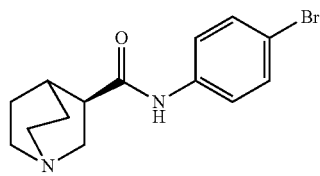 [SMILES: O=C(Nc1ccc(Br)cc1)[C@H]1CN2CCC1CC2]

9.17 g (47.8 mmol) of (R)-1-azabicyclo[2.2.2]octane-3-carboxylic acid (Example 3A) are heated together with 160 ml of thionyl chloride under reflux for 1 h. Excess thionyl chloride is removed under reduced pressure, and residues are removed by azeotropic distillation together with toluene. The acid chloride obtained in this way is stirred together with 8.19 g (47.6 mmol) of 4-bromoaniline and 24.6 ml (190.4 mmol) of N,N-diisopropylethylamine in 59 ml of DMF at RT for 72 h. The solvent is removed under reduced pressure, and the crude product is purified by chromatography on silica gel 60 (mobile phase: dichloromethane →dichloromethane/methanol/triethylamine 70:30:2). The product fractions are combined and concentrated in vacuo, and the residue is dried under high vacuum. 5.5 g (37% of theory) of the title compound are isolated. The absolute configuration was assigned by single-crystal analysis of the crystal structure.

$^1$H-NMR (200 MHz, DMSO-$d_6$): δ=10.06 (s, 1H), 7.70-7.40 (m, 4H), 3.30-3.10 (m, 1H), 2.94-2.45 (m, 6H), 2.15-2.04 (m, 1H), 1.73-1.45 (m, 3H), 1.45-1.15 (m, 1H).
HPLC (Method 1): $R_t$=3.84 min.
MS (ESIpos): m/z=309 (M+H)$^+$.

EXAMPLE 5A (3R)-Quinuclidine-3-carbonyl chloride hydrochloride

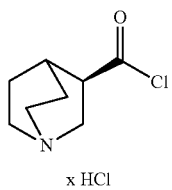 [SMILES: O=C(Cl)[C@H]1CN2CCC1CC2]

x HCl 8.18 g (64.43 mmol) of oxalyl chloride are added dropwise to a solution of 2.0 g (12.89 mmol) of (R)-1-azabicyclo[2.2.2]octane-3-carboxylic acid (Example 3A) in 10 ml of toluene. After stirring at room temperature for 18 h, the reaction mixture is concentrated in vacuo and codistilled with toluene twice. Drying under high vacuum results in 2.31 g (85.2% of theory) of the title compound, which is reacted further without further purification.

EXAMPLE 6A (3R)-N-(4'-Nitrobiphenyl-4-yl)quinuclidine-3-carboxamide hydrochloride

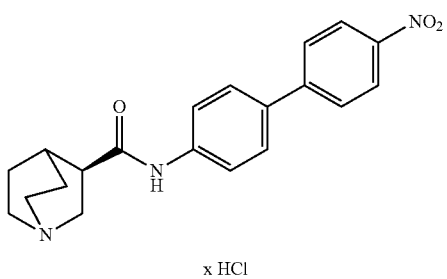 [SMILES: O=C(Nc1ccc(-c2ccc([N+](=O)[O-])cc2)cc1)[C@H]1CN2CCC1CC2]

x HCl 480 mg (3.50 mmol) of potassium carbonate are added to a mixture, prepared under argon, of 490 mg (2.33 mmol) of (3R)-quinuclidine-3-carbonyl chloride hydrochloride (Example 5A) and 250 mg (1.17 mmol) of 4-amino-4'-nitrobiphenyl in 11 ml of a 10:1 mixture of dioxane and DMF. The reaction mixture, is stirred at 100° C. for 18 h and then concentrated. The residue is suspended in methanol and filtered. The filtration residue is washed with water, mixed with 20 ml of a 3:1 mixture of acetonitrile and 1 N hydrochloric acid, again concentrated and dried under high vacuum. The above filtrate is purified by preparative HPLC. The product fractions are concentrated, taken up in 5 ml of a 3:1 mixture of acetonitrile and 1 N hydrochloric acid, again concentrated and dried under high vacuum. 291 mg (61.7% of theory) of the title compound are obtained from the filtration residue, and a further 65 mg (12.4% of theory) are obtained from the filtrate, in this way.
HPLC (Method 1): $R_t$=4.13 min.
MS (ESIpos): m/z=352 (M+H)$^+$.

EXAMPLE 7A (3R)—N-(4'-Aminobiphenyl-4-yl)quinuclidine-3-carboxamide dihydrochloride

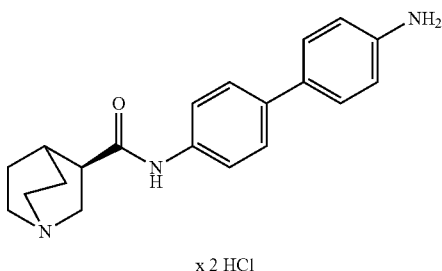 [SMILES: Nc1ccc(-c2ccc(NC(=O)[C@H]3CN4CCC3CC4)cc2)cc1]

x 2 HCl

A solution of 739 mg (2.10 mmol) of (3R)—N-(4'-nitrobiphenyl-4-yl)quinuclidine-3-carboxamide (Example 6A) in 10 ml of methanol and 5 ml of 2 N hydrochloric acid is hydrogenated under atmospheric pressure in the presence of 448 mg (0.21 mmol) of 5% palladium on carbon for 2 h. Filtration through kieselgur is followed by washing with methanol and concentration of the filtrate and drying under high vacuum. 755 mg (89.2% of theory) of the title compound are obtained.
HPLC (Method 1): $R_t$=3.04 min.
MS (ESIpos): m/z=322 (M+H)$^+$.

EXAMPLE 8A (3R)—N-(3'-Aminobiphenyl-4-yl)quinuclidine-3-carboxamide dihydrochloride

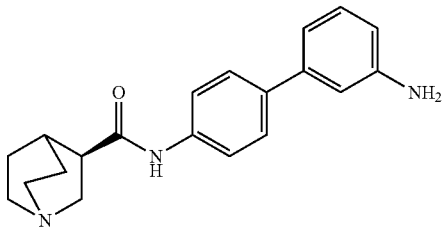

x 2 HCl

A degassed mixture of 200 mg (0.58 mmol) of (3R)—N-(4-bromophenyl)-1-azabicyclo[2.2.2]octane-3-carboxamide (Example 4A), 215.2 mg (0.58 mmol) of 3-aminophenylboronic acid hemisulfate, 579 μl (1.74 mmol) of 3 N sodium hydroxide solution and 21.2 mg (0.03 mmol) of PdCl$_2$(dppf) in 3 ml of DMF is heated at 90° C. for 18 h. Cooling to RT is followed by purification by preparative HPLC. The product fractions are concentrated, mixed with 3 ml of 1 N hydrochloric acid and again concentrated. Drying under high vacuum results in 146 mg (39.4% of theory) of the title compound, which is reacted further without further purification.

EXAMPLE 9A

N-Benzyl-4'-nitrobiphenyl-4-sulfonamide

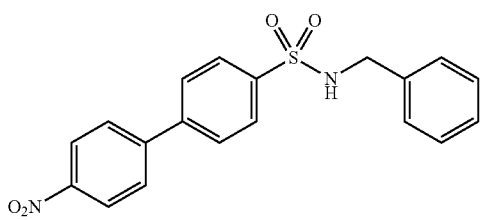

0.28 ml (2.52 mmol) of benzylamine is added to a solution of 150 mg (0.50 mmol) of 4'-nitrobiphenyl-4-sulfonyl chloride in 2.0 ml of DMF. After 18 h at room temperature, 2.5 ml of water are added to the reaction mixture. The resulting precipitate is filtered off with suction and dried under high vacuum. 159 mg (74.4% of theory) of the title compound are obtained and reacted further without further purification.
LC-MS (Method 3): R$_t$=3.83 min.; m/z=369 (M+H)$^+$.

EXAMPLE 10A

4'-Amino-N-benzylbiphenyl-4-sulfonamide

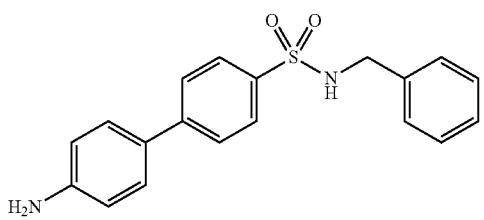 [SMILES: O=[N+]([O-])c1ccc(-c2ccc(S(=O)(=O)NCc3ccccc3)cc2)cc1]

416.5 mg (1.85 mmol) of tin(II) chloride dihydrate are added to a solution of 136 mg (0.37 mmol) of N-benzyl-4'-nitrobiphenyl-4-sulfonamide (Example 9A) in 2.0 ml of DMF. After 18 h at room temperature, the reaction mixture is purified by preparative HPLC. The product fractions are concentrated in vacuo and dried under high vacuum. 117 mg (84.3% of theory) of the title compound are obtained.
HPLC (Method 1): R$_t$=3.91 min.
MS (ESIpos): m/z=339 (M+H)$^+$.

EXAMPLE 11A

N-Isopropyl-4'-nitrobiphenyl-4-sulfonamide

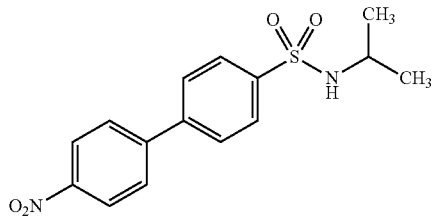

0.22 ml (2.52 mmol) of isopropylamine is added to a solution of 150 mg (0.50 mmol) of 4'-nitrobiphenyl-4-sulfonyl chloride in 2.0 ml of DMF. After 18 h at room temperature, 2.5 ml of water are added to the reaction mixture. The resulting precipitate is filtered off with suction and dried under high vacuum. 126 mg (64.4% of theory) of the title compound are obtained and reacted further without further purification.
LC-MS (Method 3): R$_t$=3.66 min.; m/z=321 (M+H)$^+$.

EXAMPLE 12A

4'-Amino-N-isopropylbiphenyl-4-sulfonamide

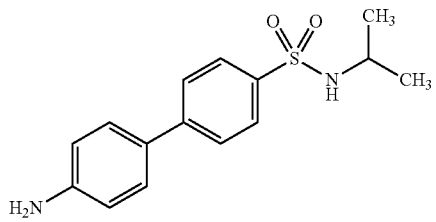 [SMILES: CC(C)NS(=O)(=O)c1ccc(-c2ccc([N+](=O)[O-])cc2)cc1]

288.8 mg (1.28 mmol) of tin(II) chloride dihydrate are added to a solution of 100 mg (0.26 mmol) of N-isopropyl-4'-nitrobiphenyl-4-sulfonamide (Example 11A) in 2.0 ml of DMF. After 18 h at room temperature, the reaction mixture is purified by preparative HPLC. The product fractions are concentrated in vacuo and dried under high vacuum. 47 mg (63.2% of theory) of the title compound are obtained.
HPLC (Method 1): R$_t$=3.57 min.
MS (DCI): m/z=291 (M−H)$^+$.

Exemplary Embodiments:

EXAMPLE 1

[(4'-{[(3R)-1-Azabicyclo[2.2.2]oct-3-ylcarbonyl]amino}biphenyl-4-yl)amino](oxo)acetic acid hydrochloride

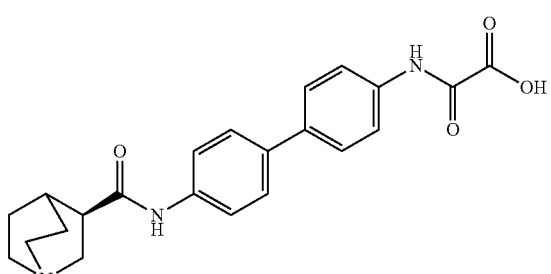

300 mg (2.14 mmol) of potassium carbonate are added to a mixture, prepared wider argon, of 300 mg (1.43 mmol) of (3R)-quinuclidine-3-carbonyl chloride hydrochloride (Example 5A) and 180 mg (0.71 mmol) of [(4'-aminobiphenyl-4-yl)amino](oxo)acetic acid [CAS Registry No. 100872-66-0] in 11 ml of a 10:1 mixture of dioxane and DMF. After 18 h at 100° C., the reaction mixture is concentrated in vacuo, and the residue is dissolved in water and acetonitrile and purified by preparative HPLC. The concentrated product fractions are mixed with 5 ml of a 2:1 mixture of acetonitrile and 1 N hydrochloric acid and again concentrated. Drying under high vacuum results in 64 mg (20.3% of theory) of the title compound.

HPLC (Method 1): $R_t$=3.40 min.
MS (ESIpos): m/z=350 (M+H)$^+$.

EXAMPLE 2

(3R)-N-{4'-[(Methylsulfonyl)amino]biphenyl-4-yl}quinuclidine-3-carboxamide hydrochloride

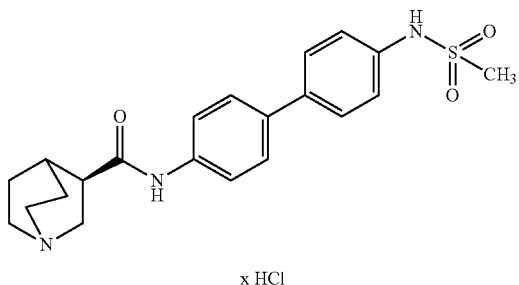 [SMILES: CS(=O)(=O)Nc1ccc(-c2ccc(NC(=O)[C@H]3CN4CCC3CC4)cc2)cc1]

x HCl 300 mg (2.14 mmol) of potassium carbonate are added to a mixture, prepared under argon, of 300 mg (1.43 mmol) of (3R)-quinuclidine-3-carbonyl chloride hydrochloride (Example 5A) and 187 mg (0.71 mmol) of N-(4'-aminobiphenyl-4-yl)methylsulfonamide [CAS Registry No. 82315-47-7] in 11 ml of a 10:1 mixture of dioxane and DMF. After 18 h at 100° C., the reaction mixture is concentrated in vacuo, and the residue is dissolved in water and acetonitrile and purified by preparative HPLC. The concentrated product fractions are mixed with 5 ml of a 2:1 mixture of acetonitrile and 1 N hydrochloric acid and again concentrated. Drying under high vacuum results in 186 mg (58.3% of theory) of the title compound.

$^1$H-NMR. (300 MHz, DMSO-d$_6$): δ=10.45 (s, 1H), 10.19 (br. s, 1H), 9.80 (s, 1H), 7.71 (m, 2H), 7.61 (m, 4H), 7.28 (m, 2H), 3.60 (dd, 1H), 3.42-3.10 (m, 6H), 3.01 (s, 3H), 2.45 (m, 1H), 1.93 (m, 2H), 1.76 (m, 2H).
HPLC (Method 1): $R_t$=3.59 min.
MS (ESIpos): m/z=400 (M+H)$^+$.

EXAMPLE 3

(3R)—N- (3'-[(Methylsulfonyl)amino]biphenyl-4-yl)quinuclidine-3-carboxamide hydrochloride

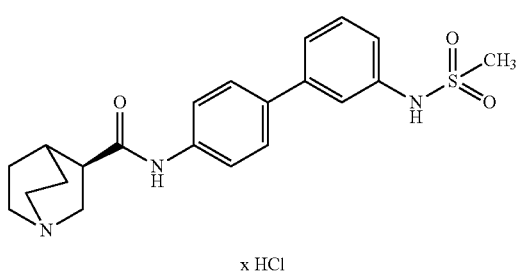 [SMILES: CS(=O)(=O)Nc1cccc(-c2ccc(NC(=O)[C@H]3CN4CCC3CC4)cc2)c1]

x HCl 63.6 μl (0.46 mmol) of triethylanaine and 21.2 μl (0.27 mmol) of methanesulfonyl chloride are added to a solution of 60 mg (0.09 mmol) of (3R)—N-(3'-aminobiphenyl-4-yl)quinuclidine-3-carboxamide dihydrochloride (Example 8A) in 1 ml of DMF at room temperature. After 18 h at room temperature, the reaction mixture is diluted with a 1:1 mixture of acetonitrile and water and purified by preparative HPLC. The product fractions are concentrated, taken up in 1 ml of 1 N hydrochloric acid, again concentrated and dried under high vacuum. 14 mg (35.2% of theory) of the title compound are obtained.

HPLC (Method 1): $R_t$=3.70 min.
LC-MS (Method 2): $R_t$=2.45 min.; m/z=400 (M+H)$^+$.

EXAMPLE 4

(3R)—N-{4'-[(Ethylsulfonyl)amino]biphenyl-4-yl}quinuclidine-3-carboxamide hydrochloride

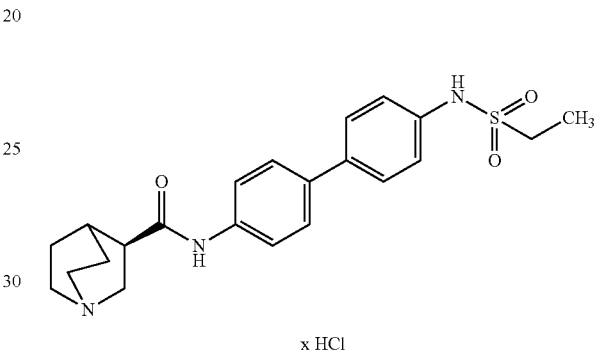

x HCl 39.1 mg (0.30 mmol) of ethanesulfonyl chloride and 84.8 μl (0.61 mmol) of tiethylamine are added to a solution of 60 mg (0.15 mmol) of ((3R)—N-(4'-aminobiphenyl-4-yl)quinuclidine-3-carboxamide dihydrochloride (Example 7A) in 0.5 ml of DMF. After 18 h at room temperature, the reaction mixture is purified by preparative HPLC. The product fractions are concentrated, mixed with 2 ml of a 1:1 mixture of acetonitrile and 1 N hydrochloric acid, again concentrated and dried under high vacuum. 26 mg (35.2% of theory) of the title compound are obtained.

HPLC (Method 1): $R_t$=3.71 min.
MS (ESIpos): m/z=414 (M+H)$^+$.

EXAMPLE 5

(3R)—N-{4'-[(Phenylsulfonyl)amino]biphenyl-4-yl}quinuclidine-3-carboxamide hydrochloride

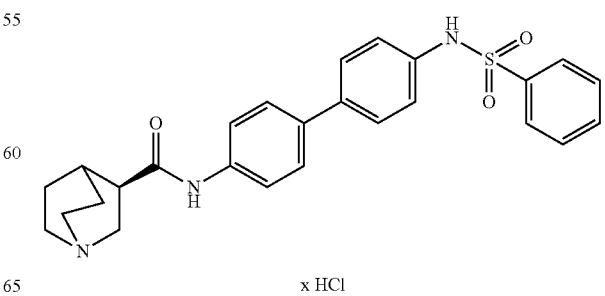

x HCl

A solution of 80 mg (0.20 mmol) of ((3R)—N-(4'-amino-biphenyl-4-yl)quinuclidine-3-carboxamide dihydrochloride (Example 7A) and 71.7 mg (0.41 mmol) of phenylsulfonyl chloride in 1.0 ml of pyridine is stirred at room temperature for 18 h. The reaction mixture is concentrated in vacuo and the residue is purified by preparative HPLC. The product fractions are concentrated, mixed with 3 ml of 1 N hydrochloric acid, again concentrated and dried under high vacuum. 52 mg (51.5%0 of theory) of the title compound are obtained.

$^1$H-NMR (400 MHz, DMSO-d$_6$): δ=10.40 (s, 1H), 10.37 (s, 1H), 9.85 (br. s, 1H), 7.80 (m, 2H), 7.66 (m, 2H), 7.63-7.49 (m, 7H), 7.17 (m, 2H), 3.61 (dd, 1H), 3.43-3.17 (m, 5H), 3.11 (m, 1H), 2.41 (m, 1H), 1.92 (m, 2H), 1.73 (m, 2H).
HPLC (Method 1): R$_t$=4.05 min.
MS (ESIpos): m/z=462 (M+H)$^+$.

EXAMPLE 6

(3R)—-N-{4'-[(Benzylsulfonyl)amino]biphenyl-4-yl)quinuclidine-3-carboxamide hydrochloride

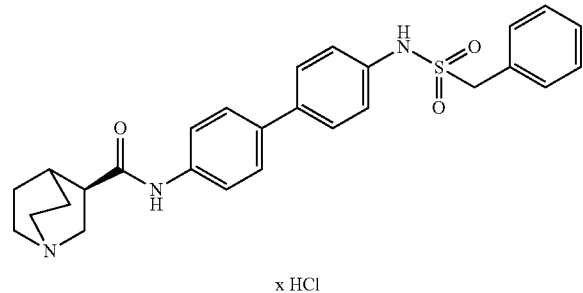 [SMILES: O=C(Nc1ccc(-c2ccc(NS(=O)(=O)Cc3ccccc3)cc2)cc1)[C@H]1CN2CCC1CC2]

x HCl

A solution of 80 mg (0.20 mmol) of ((3R)—N-(4'-amino-biphenyl-4-yl)quinuclidine-3-carboxamide dihydrochloride (Example 7A) and 77.4 mg (0.41 mmol) of phenylmethane-sulfonyl chloride in 1.0 ml of pyridine is stirred at room temperature for 18 h. The reaction mixture is concentrated in vacuo and the residue is purified by preparative HPLC. The product fractions are concentrated, mixed with 3 ml of 1 N hydrochloric acid, again concentrated and dried under high vacuum. 34 mg (32.7% of theory) of the title compound are obtained.
HPLC (Method 1): R$_t$=4.12 min.
MS (ESIpos): m/z=476 (M+H)$^+$.

EXAMPLE 7

(3R)—N-[4'-(Aminosulfonyl)biphenyl-4-yl]quinuclidine-3-carboxamide hydrochloride

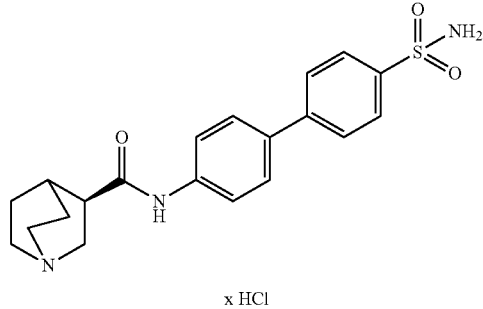 [SMILES: NS(=O)(=O)c1ccc(-c2ccc(NC(=O)[C@H]3CN4CCC3CC4)cc2)cc1]

x HCl 213.5 mg (1.54 mmol) of potassium carbonate are added to a mixture, prepared under argon, of 216.3 mg (1.03 mmol) of (3R)-quinuclidine-3-carbonyl chloride hydrochloride (Example 5A) and 127.8 mg (0.51 mmol) of (4'-amino-4-biphe-nyl)sulfonamide in 5.5 ml of a 10:1 mixture of dioxane and DMF. After 18 h at 100° C., a further 216.3 mg (1.03 mmol) of (3R)-quinuclidine-3-carbonyl chloride hydrochloride are added. After a further 18 h at 100° C., the product is precipitated by adding acetonitrile/water (2:1). Drying under high vacuum results in 148 mg (71.9% of theory) of the title compound.

$^1$H-NMR (200 MHz, DMSO-d$_6$): δ=10.06 (s, 1H), 7.92-7.80 (m, 4H), 7.79-7.68 (m, 4H), 7.39 (s, 2H), 3.22 (dd, 1H), 2.93-2.58 (m, 6H), 2.09 (m, 1H), 1.60 (m, 3H), 1.33 (m, 1H).
HPLC (Method 1): R$_t$=3.40 min.
MS (ESIpos): m/z=386 (M+H)$^+$.

EXAMPLE 8

(3R)—N-{4'-[(Isopropylamino)sulfonyl]biphenyl-4-yl}quinuclidine-3-carboxamide hydrochloride

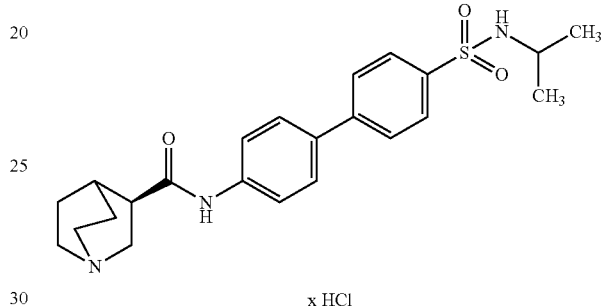

x HCl 64.3 mg (0.46 mmol) of potassium carbonate are added to a mixture, prepared under argon, of 65.1 mg (0.31 mmol) of (3R)-quinuclidine-3-carbonyl chloride hydrochloride (Example 5A) and 45.0 mg (0.15 mmol) of 4'-amino-N-isopropylbiphenyl-4-sulfonamide (Example 12A) in 2.2 ml of a 10:1 mixture of dioxane and DMF. After 18 h at 100° C., the reaction mixture is concentrated in vacuo. The residue is dissolved in water and acetonitrile and purified by preparative HPLC. The product fractions are concentrated, mixed with 5 ml of a 2:1 mixture of acetonitrile and 1 N hydrochloric acid, again concentrated and dried under high vacuum. 21 mg (29.2% of theory) of the title compound are obtained.
HPLC (Method 1): R$_t$=3.93 min.
MS (ESIpos): m/z=428 (M+H)$^+$.

EXAMPLE 9

(3R)—N-{4'-[(Benzylamino)sulfonyl]biphenyl-4-yl}quinuclidine-3-carboxamide hydrochloride

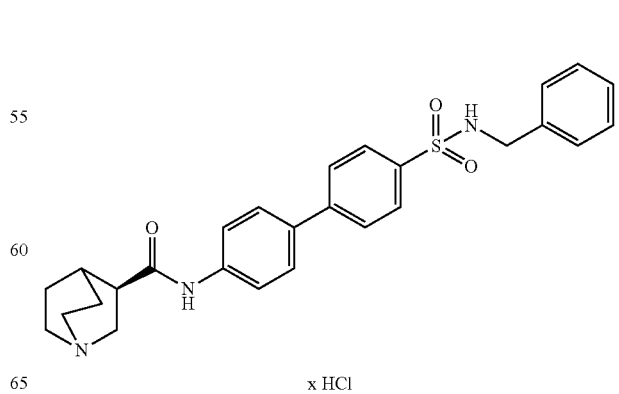

x HCl 73.5 mg (0.60 mmol) of potassium carbonate are added to a mixture, prepared under argon, of 74.5 mg (0.35 mmol) of (3R)-quinuclidine-3-carbonyl chloride hydrochloride (Example 5A) and 60 mg (0.18 mmol) of 4'-amino-N-benzylbiphenyl-4-sulfonamide (Example 10A) in 2.2 ml of a 10:1 mixture of dioxane and DMF. After 18 h at 100° C., a further 74.5 mg. (0.35 mmol) of (3R)-quinuclidine-3-carbonyl chloride hydrochloride are added. After a further 24 h at 100° C., the reaction mixture is concentrated in vacuo. The residue is dissolved in water and acetonitrile and purified by preparative HPLC. The product fractions are concentrated, mixed with 5 ml of a 2:1 mixture of acetonitrile and 1 N hydrochloric acid, again concentrated and dried under high vacuum. 64 mg (70.5% of theory) of the title compound are obtained.
HPLC (Method 1): $R_t$=4.17 min.
MS (ESIpos): m/z=476 (M+H)$^+$.

EXAMPLE 10

(3R)—N-(4'-{[(Methylamino)carbonyl]amino}biphenyl-4-yl)quinuclidine-3-carboxamide

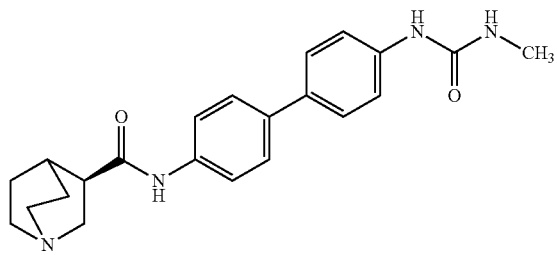 [SMILES: CNC(=O)Nc1ccc(-c2ccc(NC(=O)[C@H]3CN4CCC3CC4)cc2)cc1]

17.4 mg (0.30 mmol) of methyl isocyanate and 84.8 μl (0.61 mmol) of triethylamine are added to a solution of 60 mg (0.15 mmol) of ((3R)—N-(4'-aminobiphenyl-4-yl)quinuclidine-3-carboxamide dihydrochloride (Example 7A) in 0.5 ml of DMF. After 18 h at room temperature, 5 ml of water are added to the reaction mixture. The resulting precipitate is filtered off with suction, washed with water and dried under high vacuum. 47 mg (73.5% of theory) of the title compound are obtained.
HPLC (Method 1): $R_t$=3.44 min.
MS (ESIpos): m/z=379 (M+H)$^+$.

EXAMPLE 11

(3R)—N-(4'-{[(Cyclopentylamino)carbonyl]amino}biphenyl-4-yl)quinuclidine-3-carboxamide hydrochloride

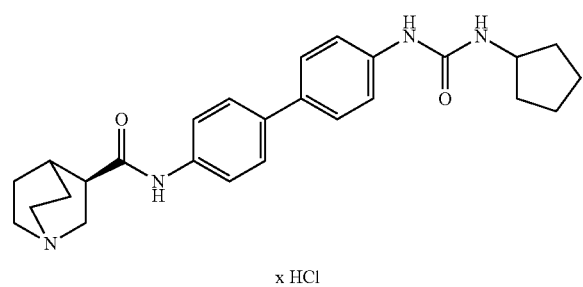 [SMILES: O=C(Nc1ccc(-c2ccc(NC(=O)[C@H]3CN4CCC3CC4)cc2)cc1)NC1CCCC1]

33.8 mg (0.30 mmol) of cyclopentyl isocyanate and 84.8 μl (0.61 mmol) of triethylamine are added to a solution of 60 mg (0.15 mmol) of ((3R)—N-(4'-aminobiphenyl-4-yl)quinuclidine-3-carboxamide dihydrochloride (Example 7A) in 0.5 ml of DMF. After 18 h at room temperature, 5 ml of water are added to the reaction mixture. The resulting precipitate is filtered off with suction, washed with water and dried under high vacuum. A preparative HPLC is carried out for further purification. The product fractions are concentrated, mixed with 3 ml of 1 N hydrochloric acid, again concentrated and dried under high vacuum. 28 mg (39.2% of theory) of the title compound are obtained.
$^1$H-NMR (300 MHz, DMSO-d$_6$): δ=10.33 (s, 1H), 9.95 (s, 11-1), 8.51 (s, 1H), 7.67 (m, 2H), 7.58 (m, 2H), 7.50 (m, 2H), 7.44 (m, 2H), 6.29 (br. S, 1H), 3.96 (m, 1H), 3.60 (m, 1H), 3.37 (m, 1H), 3.29-3.08 (m, 5H), 2.43 (m, 1H), 1.92 (m, 2H), 1.84 (m, 2H), 1.77 (m, 2H), 1.64 (m, 2H), 1.55 (m, 2H), 1.38 (m, 2H).
HPLC (Method 1): $R_t$=4.05 min.
MS (ESIpos): m/z=433 (M+H)$^+$.

EXAMPLE 12

(3R)—N-(4'-[(Ethylamino)carbonyl]amino}biphenyl-4-yl)quinuclidine-3-carboxamide

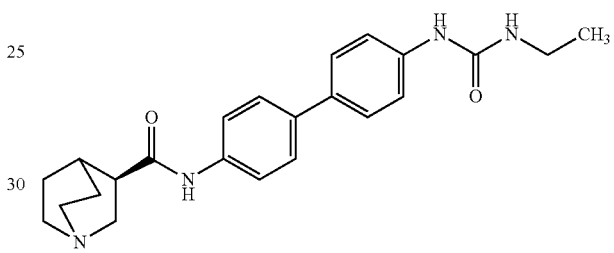

21.6 mg (0.30 mmol) of ethyl isocyanate and 84.8 μl (0.61 mmol) of triethylamine are added to a solution of 60 mg (0.15 mmol) of ((3R)—N-(4'-aminobiphenyl-4-yl)quinuclidine-3-carboxamide dihydrochloride (Example 7A) in 0.5 ml of DMF. After 18 h at room temperature, 5 ml of water are added to the reaction mixture. The resulting precipitate is filtered off with suction, washed with water and dried under high vacuum. 57 mg (88.0% of theory) of the title compound are obtained.
HPLC (Method 1): $R_t$=3.62 min.
MS (ESIpos): m/z=393 (M+H)$^+$.

EXAMPLE 13

(3R)—N-[4'-({[(3-Methoxyphenyl)amino]carbonyl}amino)biphenyl-4-yl]quinuclidine-3-carboxamide hydrochloride

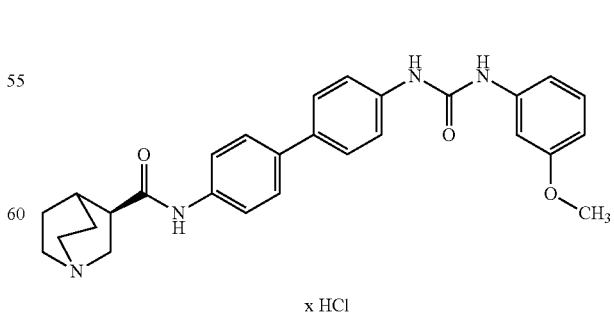

45.4 mg (0.30 mmol) of 3-methoxyphenyl isocyanate and 84.8 μl (0.61 mmol) of triethylamine are added to a solution of 60 mg (0.15 mmol) ((3R)—N-(4'-aminobiphenyl-4-yl)quinuclidine-3-carboxamide dihydrochloride (Example 7A) in 0.5 ml of DMF. After 18 h at room temperature, 5 ml of water are added to the reaction mixture. The resulting precipitate is filtered off with suction, washed with water and dried under high vacuum. A preparative HPLC is carried out for further purification. The product fractions are concentrated, mixed with 3 ml of 1 N hydrochloric acid, again concentrated and dried under high vacuum. 22 mg (27.6% of theory) of the title compound are obtained.
HPLC (Method 1): $R_t$=4.19 min.
MS (ESIpos): m/z=471 (M+H)$^+$.

EXAMPLE 14

(3R)—N-{4'-[(3-Chlorobenzoyl)amino]biphenyl-4-yl}quinuclidine-3-carboxamide hydrochloride

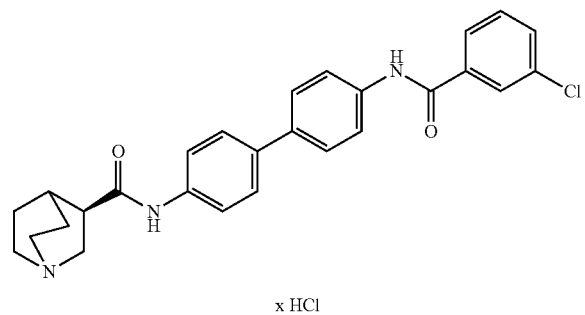 [SMILES: O=C(Nc1ccc(-c2ccc(NC(=O)[C@H]3CN4CCC3CC4)cc2)cc1)c1cccc(Cl)c1]

x HCl

A solution of 50 mg (0.13 mmol) of ((3R)—N-(4'-aminobiphenyl-4-yl)quinuclidine-3-carboxamide dihydrochloride (Example 7A) and 44.4 mg (0.25 mmol) of 3-chlorobenzoyl chloride in 1.0 ml of pyridine is stirred at room temperature for 3 h. The reaction mixture is concentrated in vacuo, and the residue is purified by preparative HPLC. The product fractions are concentrated, mixed with 3 ml of 1 N hydrochloric acid, again concentrated and dried under high vacuum. 62 mg (98.5% of theory) of the title compound are obtained.
HPLC (Method 1): $R_t$=4.41 min.
MS (ESIpos): m/z=460 (M+H)$^+$.

EXAMPLE 15

(3R)—N-{4'-[(3-Fluorobenzoyl)amino]biphenyl-4-yl}quinuclidine-3-carboxamide hydrochloride

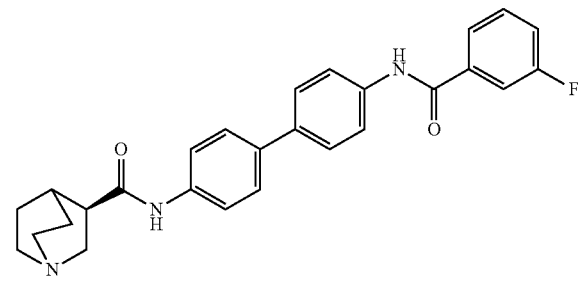

x HCl

A solution of 50 mg (0.13 mmol) of ((3R)—N-(4'-aminobiphenyl-4-yl)quinuclidine-3-carboxamide dihydrochloride (Example 7A) and 40.2 mg (0.25 mmol) of 3-fluorobenzoyl chloride in 1.0 ml of pyridine is stirred at room temperature for 3 h. The reaction mixture is concentrated in vacuo, and the residue is purified by preparative HPLC. The product fractions are concentrated, mixed with 3 ml of 1 N hydrochloric acid, again concentrated and dried under high vacuum. 48 mg (73.4% of theory) of the title compound are obtained.
$^1$H-NMR (200 MHz, DMSO-d$_6$): δ=10.48 (s, 1H), 10.43 (s, 1H), 10.21 (br. s, 1H), 7.92-7.80 (m, 3H), 7.79-7.57 (m, 8H), 7.49 (m, 1H), 3.61 (m, 1H), 3.44-3.08 (m, 6H), 2.46 (m, 1H), 1.92 (n, 2H), 1.75 (m, 2H).
HPLC (Method 1): $R_t$=4.21 min.
MS (ESIpos): m/z=444 (M+H)$^+$.

EXAMPLE 16

(3R)—N-{4'-[(2-Methoxyacetyl)amino]biphenyl-4-yl}quinuclidine-3-carboxamide hydrochloride

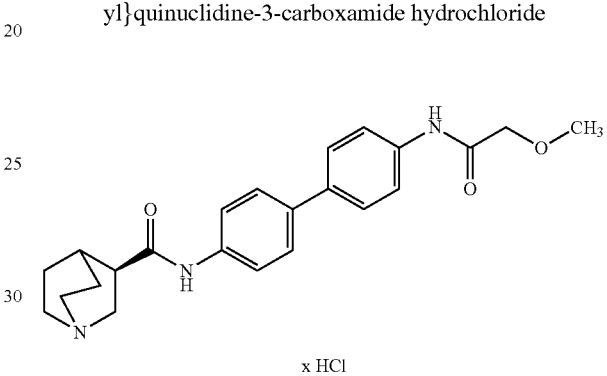

x HCl

A solution of 50 mg (0.13 mmol) of ((3R)—N-(4'-aminobiphenyl-4-yl)quinuclidine-3-carboxamide dihydrochloride (Example 7A) and 27.5 mg (0.25 mmol) of methoxyacetyl Chloride in 1.0 ml of pyridine is stirred at room temperature for 18 h. The reaction mixture is mixed with 3 ml of DMSO and purified by preparative HPLC. The product fractions are concentrated, mixed with 5 ml of 1 N hydrochloric acid, again concentrated and dried under high vacuum. 16 mg (29.4% of theory) of the title compound are obtained.
HPLC (Method 1): $R_t$=163 min.
MS (ESIpos): m/z=394 (M+H)$^+$.

EXAMPLE 17

(3R)—N-(4'-[(Cyclopentylcarbonyl)amino]biphenyl-4-yl}quinuclidine-3-carboxamide hydrochloride

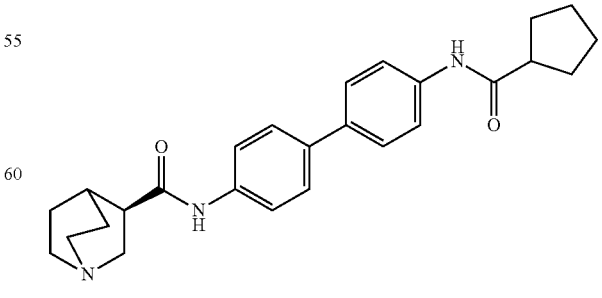

x HCl

A solution of 50 mg (0.13 mmol) of ((3R)—N-(4'-amino-biphenyl-4-yl)quinuclidine-3-carboxamide dihydrochloride (Example 7A) and 38.5 µl (0.32 mmol) of cyclopentanecarbonyl chloride in 1.0 ml of pyridine is stirred at room temperature for 18 h. The reaction mixture is mixed with 3 ml of DMSO and purified by preparative HPLC. The product fractions are concentrated, mixed with 5 ml of 1 N hydrochloric acid, again concentrated and dried under high vacuum. 22 mg (38.2% of theory) of the title compound are obtained.
HPLC (Method 1): $R_t$=4.18 min.
MS (ESIpos): m/z=418 (M+H)$^+$.

What is claimed is:

1. A method for treating cognitive impairment in a patient suffering from Alzheimer's disease or schizophrenia comprising administering to the subject a compound of the formula:

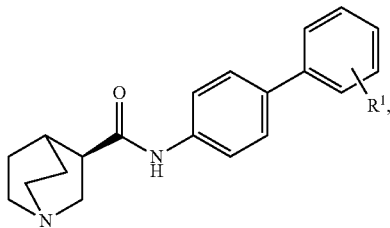

(I)

in a pharmaceutically effective amount,
in which
R$^1$ is a group of the formula —NR$^2$—CO—NR$^3$R$^4$, —NR$^2$—CO—CO—OR$^5$, —NH—SO$_2$R$^6$, —SO$_2$NHR$^7$ or —NH—CO—R$^8$, where R$^2$ is hydrogen or C$_1$-C$_6$-alkyl,
R$^3$ and R$^4$ are independently of one another hydrogen, C$_1$-C$_6$-alkyl, C$_3$-C$_8$-cycloalkyl or phenyl, which is optionally substituted by up to 3 radicals independently of one another selected from the group of halogen, cyano, C$_1$-C$_6$-alkyl, C$_1$-C$_6$-alkoxy, trifluoromethyl and trifluoromethoxy, or
R$^3$ and R$^4$ together with the nitrogen atom to which they are bonded form a 5- to 6-membered heterocyclyl,
R$^5$ is hydrogen, C$_1$-C$_6$-alkyl, C$_3$-C$_8$-cycloalkyl or aryl, where C$_1$-C$_6$-alkyl is optionally substituted by aryl,
R$^6$ is C$_1$-C$_6$-alkyl, C$_3$-C$_8$-cycloalkyl, 5- to 6-membered heterocyclyl, aryl or 5- to 6-membered heteroaryl, where C$_1$-C$_6$-alkyl is optionally substituted by aryl,
R$^7$ is hydrogen, C$_1$-C$_6$-alkyl, C$_3$-C$_8$-cycloalkyl, 5- to 6-membered heterocyclyl, aryl or 5- to 6-membered heteroaryl, where C$_1$-C$_6$-alkyl is optionally substituted by aryl,
R$^8$ is C$_3$-C$_8$-cycloalkyl, C$_1$-C$_6$-alkyl or phenyl, where C$_1$-C$_6$-alkyl is substituted by C$_1$-C$_6$-alkoxy and phenyl by 1 to 3 radicals independently of one another selected from the group of halogen, cyano, C$_1$-C$_6$-alkyl, C$_1$-C$_6$-alkoxy, trifluoromethyl and trifluoromethoxy, or a salt thereof.

2. The method of claim 1, wherein the cognitive impairment is Alzheimer's disease.

3. The method of claim 1 wherein the cognitive impairment is schizophrenia.

4. The method of claim 1, further comprising co-administering a second active ingredient for the treatment of the cognitive impairment.

5. The method of claim 1, wherein the administering is by an oral, transdermal, parenteral or inhalation route.

* * * * *